US012564325B2

(12) United States Patent
Al-Saffar et al.

(10) Patent No.: US 12,564,325 B2
(45) Date of Patent: Mar. 3, 2026

(54) ELECTROMAGNETIC IMAGING APPARATUS AND PROCESS

(71) Applicant: EMvision Medical Devices Ltd, Brisbane (AU)

(72) Inventors: Ahmed Al-Saffar, Brisbane (AU); Amin Abbosh, Brisbane (AU)

(73) Assignee: EMvision Medical Devices Ltd, Brisbane (AU)

( * ) Notice: Subject to any disclaimer, the term of this patent is extended or adjusted under 35 U.S.C. 154(b) by 0 days.

(21) Appl. No.: 18/692,727

(22) PCT Filed: Sep. 17, 2021

(86) PCT No.: PCT/AU2021/051082
§ 371 (c)(1),
(2) Date: Mar. 15, 2024

(87) PCT Pub. No.: WO2023/039626
PCT Pub. Date: Mar. 23, 2023

(65) Prior Publication Data
US 2024/0374142 A1 Nov. 14, 2024

(51) Int. Cl.
*A61B 5/00* (2006.01)
*A61B 5/0507* (2021.01)

(52) U.S. Cl.
CPC .......... *A61B 5/0042* (2013.01); *A61B 5/0507* (2013.01); *A61B 5/7264* (2013.01); *A61B 2562/0228* (2013.01); *A61B 2562/046* (2013.01)

(58) Field of Classification Search
CPC .................................................. A61B 5/0042
See application file for complete search history.

(56) References Cited

FOREIGN PATENT DOCUMENTS

| WO | 2018098387 A1 | 5/2018 |
| WO | 2020047599 A1 | 3/2020 |

OTHER PUBLICATIONS

Hassani, A YOLOv3 Deep Neural Network Model to Detect Brain Tumor in Portable Electromagnetic Imaging System, IEEE, Jun. 2021 (Year: 2021).*
Zhou"Graph Neural Networks:A Review of Methods and Applications" 2019 (Year: 2019).*

(Continued)

*Primary Examiner* — Joseph M Santos Rodriguez
(74) *Attorney, Agent, or Firm* — Sterne, Kessler, Goldstein & Fox P.L.L.C.

(57) ABSTRACT
A computer-implemented process for electromagnetic imaging, the process including the steps of: accessing scattering data representing measurements of electromagnetic wave scattering by internal features of an object, each said measurement representing scattering of electromagnetic waves emitted by a corresponding antenna of an array of antennas disposed about an imaging domain containing at least a portion of the object, and as measured by a corresponding antenna of the array of antennas; and processing the scattering data to generate image data representing a spatial location and size of at least one internal feature of the object within the imaging domain; wherein the processing includes applying a trained message-passing graph neural network (GNN) to a graph of nodes representing spatial locations of the antennas and edges representing the measurements.

15 Claims, 12 Drawing Sheets

(56)                References Cited

OTHER PUBLICATIONS

Abbosh, A. et al., "Graph Attention Network for Microwave Imaging of Brian Anomaly" IEEE Journal of Electromagnetics, RF and Microwaves in Medicine and Biology, 7 pages (Aug. 2021).

International Search Report for International Application No. PCT/AU2021/051082, Australian Patent Office, Australia mailed on Nov. 25, 2021 4 pages.

Hossain, A et al., "A YOLOv3 Deep Neural Network Model to Detect Brain Tumor in Portable Electromagnetic Imaging System" IEEE Access, vol. 9, pp. 14 Pages, Jun. 4, 2021.

Zhou, Jet al., "Graph Neural Networks: A review of methods and applications", AI Open vol. 1, 2020, 28 Pages Apr. 8, 2021.

\* cited by examiner

ELECTROMAGNETIC IMAGING APPARATUS AND PROCESS

CROSS REFERENCE TO RELATED APPLICATIONS

The present application claims priority under 35 U.S.C. § 371 to International Patent Application No. PCT/AU2021/051082, filed Sep. 17, 2021, the content of which is hereby incorporated by reference in its entirety.

TECHNICAL FIELD

The present invention relates to electromagnetic imaging technology, and in particular to an electromagnetic imaging apparatus and process.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Whilst magnetic resonance imaging (MRI) and computed tomography (CT) are gold standard medical imaging modalities, they are very expensive, limited in number for a given community, bulky and non-portable for emergency situations, and take a very long time (typically up to about 40 min) to prepare and scan the patient. Accordingly, electromagnetic based imaging, localization and classification of stroke and other pathologies has been widely studied in the literature as a much more affordable, readily available and portable imaging alternative. Low-power electromagnetic based imaging (at frequencies from 100 MHz and typically up to no more than 4 GHz) is of particular interest because the shorter wavelength electromagnetic fields can penetrate further into the human head and produce images with higher spatial resolution than electromagnetic fields with frequencies below 100 MHz.

Research studies are performed utilizing antenna arrays, wherein each antenna has a corresponding dedicated and independent electronic transmit-receive channel to enable the collection of an entire matrix of measured scattering parameters, typically but not always being S-parameters or Z-parameters. For example, for each frequency point in a spectrum of frequencies, the $S_{ii}$ and $S_{ij}$-parameters can be directly collected by a vector network analyzer and stored as a 2-dimensional N×N matrix, where N is the number of channels and antennas in the array. In the remainder of this specification, S-parameter measurements are used as representative examples of scattering parameters, although it should be understood that other types of electromagnetic scattering measurements known to those skilled in the art, such as Z-parameters for example, can be used instead of or in addition to S-parameters.

The antennas can be wide and varied in configuration and style, for instance often taking the form of dielectrically loaded waveguides or patch antennas. The size of the antennas determines both the number of antennas that can be fitted around the head or other body part, as well as the frequency bandwidth over which the antennas are able to operate. For example in the case of the human head imaging, typically the antennas are arranged circumferentially around the head, with each pointing towards the head. Normally, a coupling medium is inserted between the antenna aperture and the head surface in order to reduce the impedance mismatch and power reflection.

In the case of stroke disease, strokes typically occur in one of two types: (i) hemorrhagic or (ii) ischemic. A hemorrhagic stroke is a type of stroke wherein a blood vessel has ruptured, causing uncontrollable bleeding into normal tissue regions, often resulting in substantial intracranial pressure, and leading to partial/complete disability, coma, or death. Similarly dangerous is the ischemic stroke, wherein a small (blood) clot has blocked blood flow to a certain part of the brain. This type of stroke is typically below the spatial resolution of microwave imaging, and is usually not immediately visible and differentiable from normal tissue, even on MRI and CT scans. However, the loss of a fresh blood supply means that the surrounding tissue will have a lower water content and can cause tissue death. The electromagnetic dielectric properties (electrical conductivity and relative permittivity) of an ischemic stroke at this stage are known to be approximately 5-20% lower than the head-average dielectric properties of healthy tissue, and consequently provide a contrast with respect to the neighboring healthy tissue. Additionally, over several hours or days, as a water-based oedema forms around the clot occlusion, an ischemic stroke provides dielectric properties higher than the hemorrhagic stroke. Each of these states and classes of strokes provides different magnitude and phase information, and can be detected using microwave imaging technology.

To image such diseases using electromagnetic medical imaging, tomographic imaging methods have traditionally been used, relying on electromagnetic field solvers based on Maxwell's field equations or variants of the same implemented on a high-speed computer. These electromagnetic field solvers are often called 'forward' or 'inverse' solvers, and are used in conjunction with the S-parameter measurements as part of the objective function to iteratively optimize a calculated electromagnetic field so that it matches that of the real-world case. There are vast numbers of such algorithms, which are often based on local/global integral or differential tomographic models, often containing Born iterative solvers. Normally the outputs of such optimizations are spatial maps of electrical conductivity and relative permittivity of tissue, often (roughly) indicating the distribution of dielectric properties of the target (i.e., abnormal) tissue, which may or may not be easily visible and differentiated from the surrounding dielectric distribution of normal tissue. In addition, tomographic methods need to solve for orders of magnitude larger number of unknowns than the number of known measurements (e.g., such as for example 10,000 unknowns in a 100×100 2D tomographic image, whereas the number of measurements is for example only 169 given an array of 14 antennas). Incidentally, tomographic methods suffer from the real possibility that the final imaging result may not converge despite using the best optimization solvers.

Another common characteristic of the tomographic methods mentioned above is a typically long computational time, even with 2D assumptions (i.e., the subject's anatomy is assumed to be invariant with respect to the z-direction as the third spatial dimension). For example, the computations usually require a wall clock time of several minutes at a minimum, and even hours in cases requiring a high isotropic image spatial resolution (such as 1 mm or 2 mm for example) to ensure accuracy. Accordingly, a 3D tomographic modelling system may be practically infeasible because the number of voxels increases as the third power of the spatial resolution, and the number of additional electromagnetic tensor field components increases three-fold to a maximum of nine. This would then require substantial investments in supercomputing power (both in terms of the number of CPUs and the amount of RAM), and any tomographic techniques based on, for example, the method of moments (MoM), finite difference time domain (FDTD) or finite element methods (FEM) would require sophisticated parallel computing algorithms, which may not necessarily provide the desired/required computation acceleration (especially for emergency case situations of stroke, for instance), despite the large computing resource investment.

Furthermore, radar-based imaging methods require an accurate estimation of the effective dielectric properties of the imaged domain, which are not known without having an MRI or CT scan of that domain. Finally, all radar based methods require a significant dielectric contrast between the abnormality and the other (i.e., healthy) tissues within the domain.

In order to circumvent the above difficulties, data-driven methods have recently been investigated as an alternative to physics-based methods. In particular, machine learning is a convenient approach to microwave imaging problems. However, despite the promise of data-driven methods, there remains room for improvement.

It is desired, therefore, to overcome or alleviate one or more difficulties of the prior art, or to at least provide a useful alternative.

SUMMARY

In accordance with some embodiments of the present invention, there is provided a computer-implemented process for electromagnetic imaging, the process including the steps of:

accessing scattering data representing measurements of electromagnetic wave scattering by internal features of an object, each said measurement representing scattering of electromagnetic waves emitted by a corresponding antenna of an array of antennas disposed about an imaging domain containing at least a portion of the object, and as measured by a corresponding antenna of the array of antennas; and processing the scattering data to generate image data representing a spatial location and size of at least one internal feature of the object within the imaging domain;

wherein the processing includes applying a trained message-passing graph neural network (GNN) to a graph of nodes representing spatial locations of the antennas and edges representing the measurements.

In some embodiments, the step of applying the GNN includes summarizing the edges of the graph to reduce their number.

In some embodiments, the step of applying the GNN includes generating weights for messages of the graph by applying an attention mechanism to the messages, each message representing a corresponding pair of nodes of the graph and a corresponding edge for the pair of nodes.

In some embodiments, the step of applying the GNN includes applying an update function to weighted messages of the graph to generate inferred labels for nodes of the graph.

In some embodiments, the inferred label for each node represents quantitative measures of degrees of overlap between the internal feature of the object and respective lines joining the corresponding antenna to respective others of the antennas.

In some embodiments, the step of processing includes generating a plurality of partial images of the internal feature of the object for respective nodes of the graph, and combining the partial images to generate the image data.

In some embodiments, each of the partial images represents one or more inferred measures of electromagnetic wave scattering by the at least one internal feature of the object for a corresponding transmitting one of the antennas and one or more respective others of the antennas for which the respective degrees of overlap are inferred to be greater than zero.

In some embodiments, each of the partial images is generated by determining, for each pair of the corresponding transmitting antenna and a corresponding one of the one or more others of the antennas, a corresponding geometric sector within the imaging domain weighted by the corresponding degree of overlap, and generating the partial image by combining the one or more weighted geometric sectors for the transmitting antenna.

In accordance with some embodiments of the present invention, there is provided a computer-readable storage medium having stored thereon executable instructions that, when executed by at least one processor, cause the at least one processor to execute any one of the above processes.

In accordance with some embodiments of the present invention, there is provided an electromagnetic imaging apparatus having components configured to execute any one of the above processes.

In accordance with some embodiments of the present invention, there is provided an electromagnetic imaging apparatus, including:

an array of antennas configured to define an imaging domain for receiving an object to be imaged; and at least one processor configured to:

access scattering data representing measurements of electromagnetic wave scattering by internal features of an object, each said measurement representing scattering of electromagnetic waves emitted by a corresponding antenna of an array of antennas disposed about an imaging domain containing at least a portion of the object, and as measured by a corresponding antenna of the array of antennas; and process the scattering data to generate image data representing a spatial distribution of at least one internal feature of the object;

wherein the processing includes applying a trained message-passing graph neural network (GNN) to a graph of nodes representing spatial locations of the antennas and edges representing the measurements.

In some embodiments, the step of applying the GNN includes summarizing the edges of the graph to reduce their number.

In some embodiments, the step of applying the GNN includes generating weights for messages of the graph by applying an attention mechanism to the messages, each message representing a corresponding pair of nodes of the graph and a corresponding edge for the pair of nodes.

In some embodiments, the step of applying the GNN includes applying an update function to weighted messages of the graph to generate inferred labels for nodes of the graph, wherein the inferred label for each node represents quantitative measures of degrees of overlap between the internal feature of the object and respective lines joining the corresponding antenna to respective others of the antennas.

In some embodiments, the step of processing includes generating a plurality of partial images of the internal feature of the object for respective nodes of the graph, and combining the partial images to generate the image data.

BRIEF DESCRIPTION OF THE DRAWINGS

Some embodiments of the present invention are hereinafter described, by way of example only, with reference to the accompanying drawings, wherein.

DETAILED DESCRIPTION

The inventors have identified a major shortcoming of prior art microwave imaging models that none of them makes use of prior knowledge about the antenna array configuration-particularly the pure data-driven ones, as opposed to the hybrid ones that incorporate physics-based solvers in one way or the other. Ignoring such information in essence amounts to treating the problem as a black-box, using little if any prior information and simply relying on more data to learn what is required to infer the response variable. Almost invariably, in practical applications such a requirement either cannot be satisfied, or is exorbitant in the best scenarios, e.g., any biomedical application.

Figure 1:
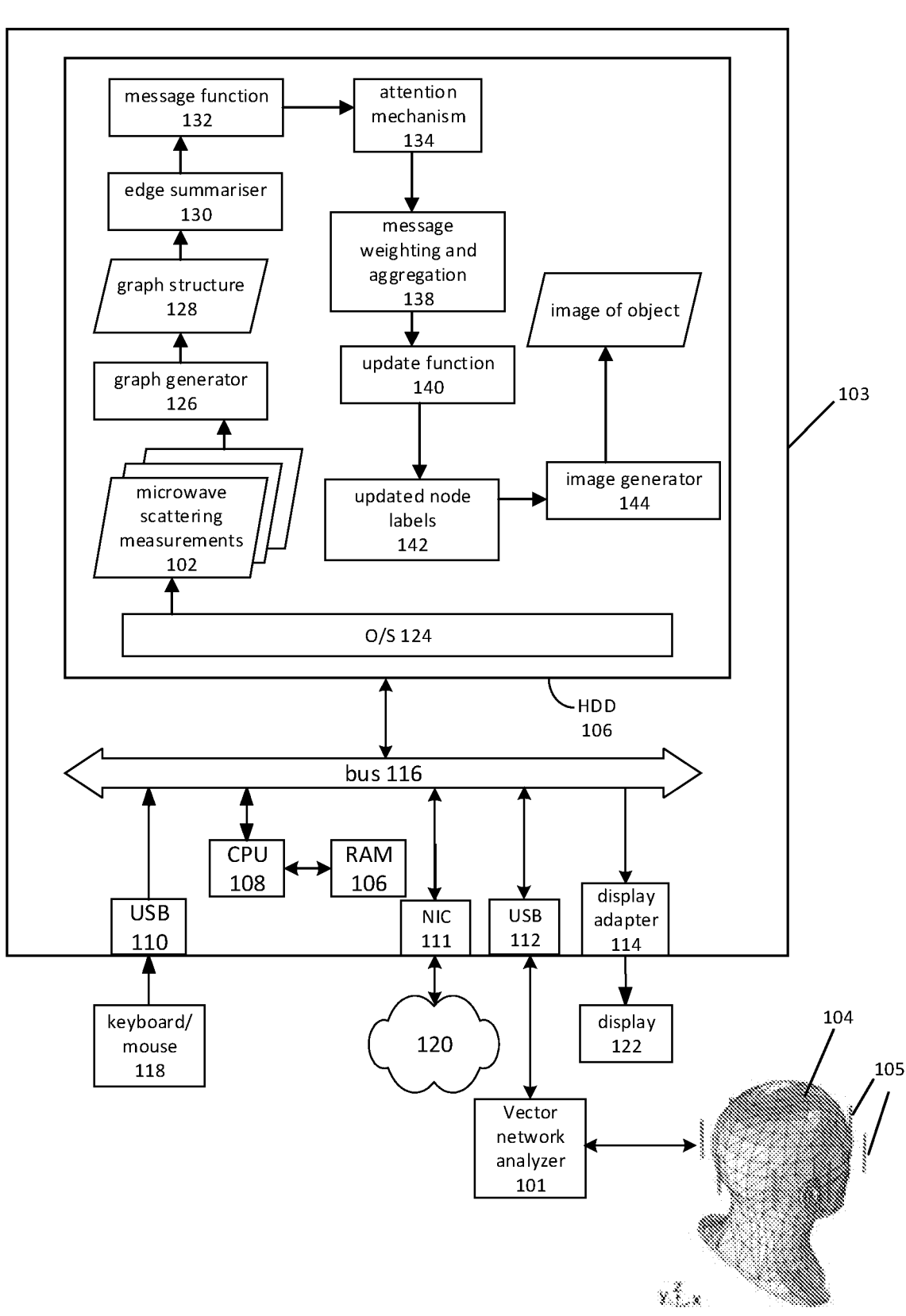
FIG. 1 is a block diagram of an electromagnetic imaging apparatus in accordance with an embodiment of the present invention.
Figure 2:
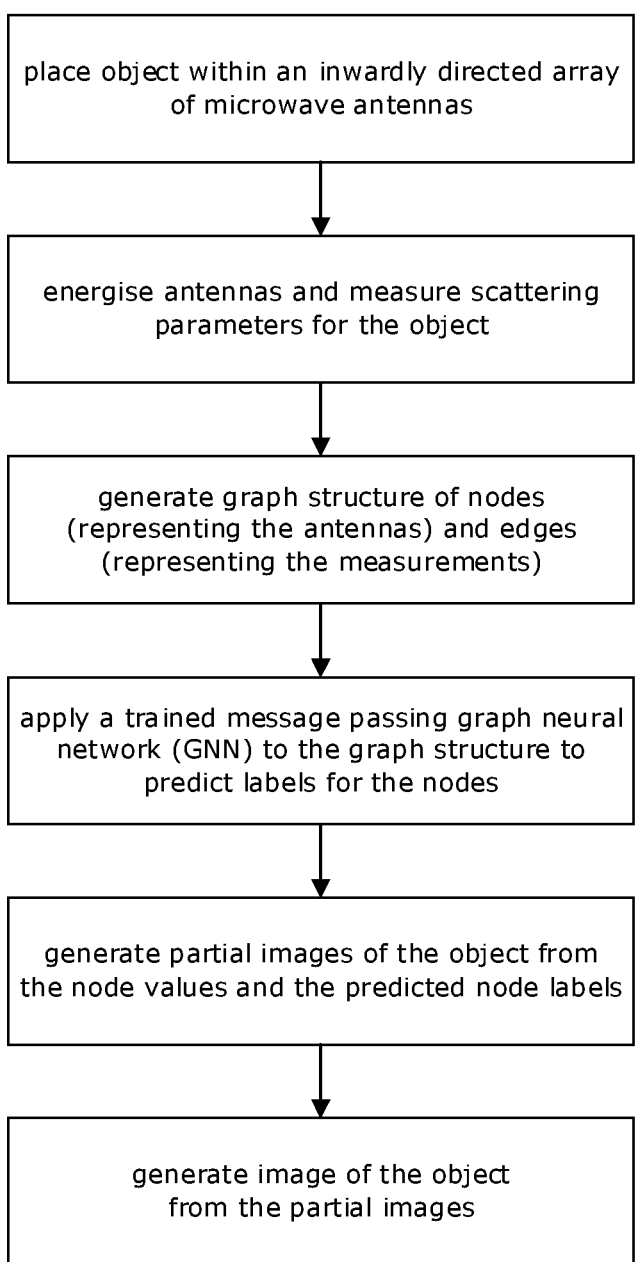
FIG. 2 is a flow diagram of an electromagnetic imaging process in accordance with an embodiment of the present invention.
Figure 3:
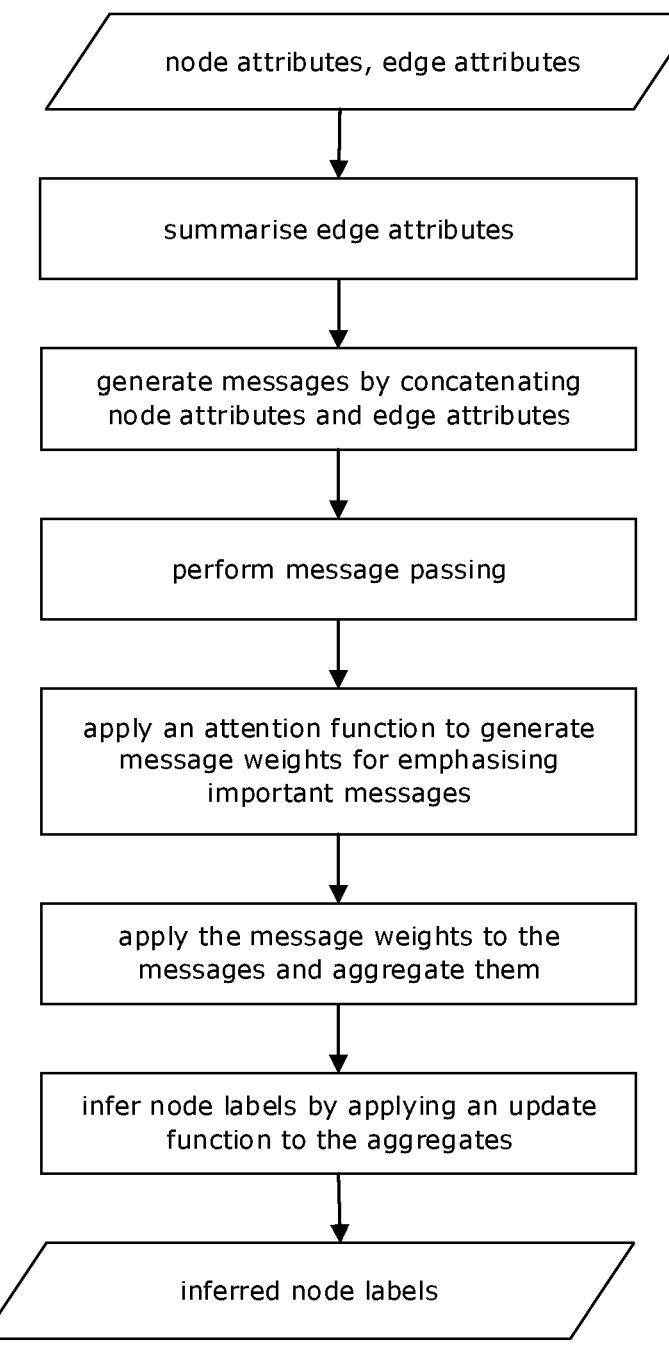
FIG. 3 is a flow diagram of a graph neural network process of the electromagnetic imaging process.

In order to address this shortcoming, the inventors have developed an apparatus and process for microwave imaging, as shown in FIGS. 1 to 3, wherein the spatial locations of the microwave imaging antennas are represented by attributes of respective nodes of a graph structure, the scattering parameters measured by the antennas are represented by corresponding edges of the graph structure, and a type of machine learning known in the art as a Graph Neural Network ("GNN") is applied to the graph.

Figure 4:
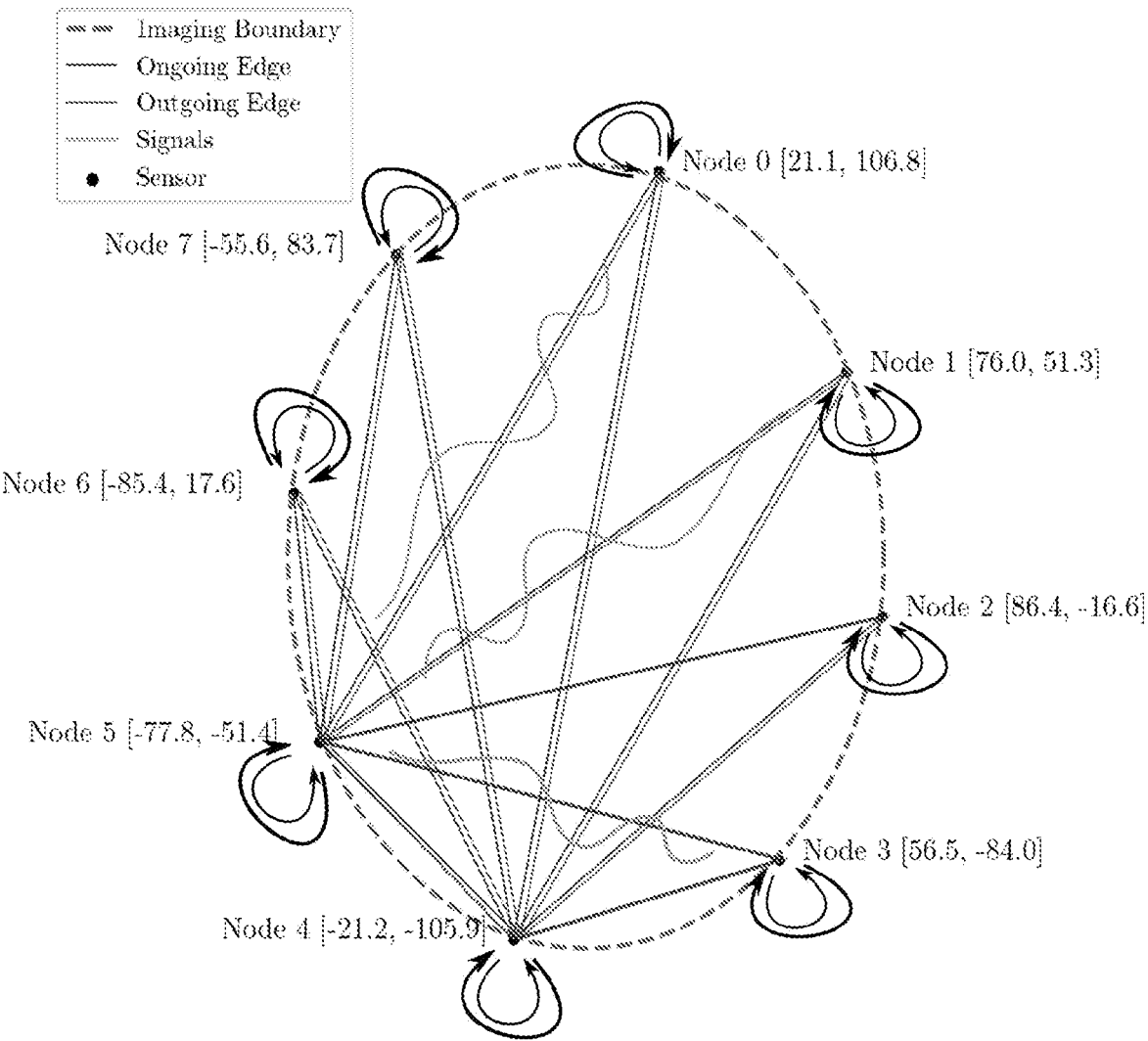
FIG. 4 is a schematic plan view of an array of electromagnetic imaging antennas disposed about an elliptical imaging domain, and illustrating a graph representation of the array wherein each antenna is represented by a corresponding node of the graph with values representing the spatial location of the antenna, and the graph's edges between pairs of nodes represent the measured scattering parameters for that period of nodes, for which one node is a transmitter and the other a receiver, only full edges for nodes 4 and 5 being shown for simplicity.

The representation of microwave imaging array as a graph allows physically meaningful connections and relations between the scattering parameter measurements to be encoded in the graph, as shown in FIG. 4. This is in stark contrast to the prior art holistic approach where the entire data captured is stacked together as one block and fed to a bulky model to infer the required response variable. Although the latter approach may work, it is data-intensive. More specifically, datasets in the order of tens of thousands of examples are common in the literature (usually compiled from simplified 2D simulations). Additionally, as the size of the imaging array increases, such holistic models bloat further and become less practical. In contrast, a graph model that utilizes the symmetry of transmitters and receivers will experience no change in size.

In the graph model described herein, the topology of the antenna array and the measurements is captured by representing the sensors (antennas) by the nodes of the graph, and the relationships between the antennas by the edges between nodes. In the described embodiments, the antenna locations are used as node attributes, and the time domain scattering parameters signals are used as edge attributes. Upon construction of such a graph, a number of inferences types can be made to solve many tasks using graphical models, although for imaging purposes, the focus will be on node-level predictions. If the imaging system is multi-static, then the graph is fully connected, which makes it difficult to infer over because it carries no specific structure and is not decomposable. To address these challenges, the GNN operations of graph convolution and attention mechanism are used to emphasise relevant messages from neighbours, and a single message passing round is sufficient to propagate all messages across the graph.

In general, a multi-static imaging apparatus of N sources captures scattering parameters over a range of useful frequencies, resulting in an N×N×F tensor, where F is the number of frequency samples captured. Thus, the graph is generated with N nodes corresponding to the respective antennas, as shown in FIG. 4. If the array is rigid, then the nodes have fixed features that correspond to the physical locations of the respective antennas. Given that the imaging apparatus is multi-static, the nodes are fully connected. Additionally, the reciprocity property of the antenna array translates to double edges between any two nodes, or equivalently an undirected graph can be constructed as an alternative. In either case, the edges of the graph are provided with attributes (also referred to as features) corresponding to the signals measured for the pairs of nodes, as shown in FIG. 4.

Across the dataset, the graph structure remains unchanged. The only variables are the measured scattering parameters; i.e., the edge features.

Having generated a graph structure representing the measured scattering parameters, the corresponding labels are identified before generating a graphical model. Predictions on GNNs can be made at graph-level, node-level or edge-level. While graph-level predictions might seem to be a reasonable choice for an imaging problem, in the described embodiments partial images are predicted at node-level before being aggregated to generate the final inferred image.

The rationale behind predicting partial images at node-level is to provide a practical balance between an overfitting-prune design predisposed to produce training-set-like solutions, and an overly flexible design that does not make use of the problem structure. The former approach optimizes for the final solution in a direct way, and is therefore rigid, fragile and holistic. Conversely, the latter approach is overly relaxed and does not recognise mutual information. A graph-level prediction of a GNN would be an example of the former as the optimization will reference the final image in a direct way. An example of the latter is a method known as Delay-Multiply And Sum (or "DMAS"), also known as "Confocal Imaging", in which an independent partial solution is generated for each antenna, and an overall solution is generated by aggregating these partial solutions. An important consequence of this approach is that the overall solution is flexible enough to capture any shape. However, it doesn't make use of mutual information between signals, which is important in a noisy environment.

As a compromise between these two ends of the spectrum, in the described embodiments the GNN generates a partial-solution per-node, as opposed to, per-signal or edge (as in DMAS). In this way, the model makes use of mutual information between all of the signals received by a single node (antenna), while remaining flexible enough to allow for prediction of arbitrary shapes following the aggregations of the per-node partial solutions. Thus, for an imaging array with N sensors, exactly N partial solutions are generated, as opposed to the N*N partial solutions of DMAS or only 1 solution in case of graph-level inference.

Node-Level Labels From Ground Truth Images

Figure 5:
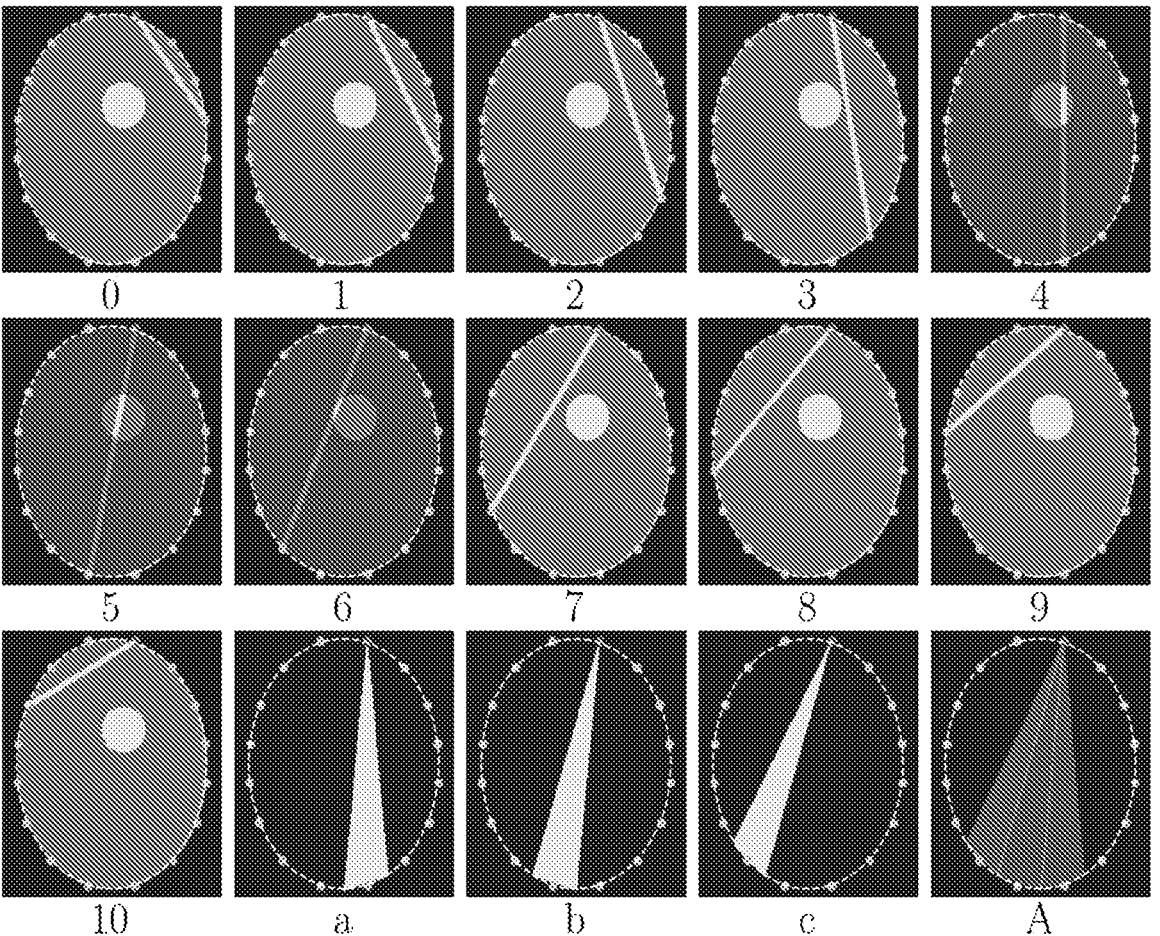
FIG. 5 is an array of schematic plan view images of an array of 16 antennas, illustrating processes for encoding and decoding node-level labels for a single node from a training image of an object containing an anomaly (yellow circle), wherein a vector of values quantifies the degree of overlap of a line joining the single antenna/node with the other antenna/nodes of the array (images 0 to 10); the resulting vector is used for training, and at inference time a vector of these values is inferred and used to generate a corresponding image by converting the non-zero values of the vector to respective geometric sectors (images a, b, and c) that are aggregated to form a partial image (image A), the partial images for all nodes of the array being combined to generate an image of the object.

In order to generate node-level labels for training the GNN, any type of image of a known target (e.g., abnormal tissue) is converted to partial images that reflect the perspective of individual nodes (antennas), as follows. As shown in FIG. 5, for each node (i), lines connecting the node of interest (i) to every other node (j) are generated. For each of these lines, if the line overlaps the target region, then a numerical value proportional to the length of the overlapping portion of the line is assigned to that line as a weight. The resulting weights are then aggregated into a vector of length N for the node. This vector is referred to as the 'label' of the node. A visualization of this procedure for a single node is illustrated (for all but the closest two nodes on either side of the single node) in images 0 to 10 of FIG. 5. These steps are repeated for every other node in the graph until all of the node-level labels or codes are generated. The labels are used to train the GNN, as described below.

The resulting labels represent what the trained GNN is to directly infer at each node, and an image of a target can be generated from the labels/codes predicted by the model. In the described embodiment, this is achieved by generating directed sectors, as shown in images a, b, and c of FIG. 4, that are weighted by the respective code/label values and aggregated to generate a partial-solution image from the perspective of the node of interest, as shown in image A of FIG. 5.

Figure 6:
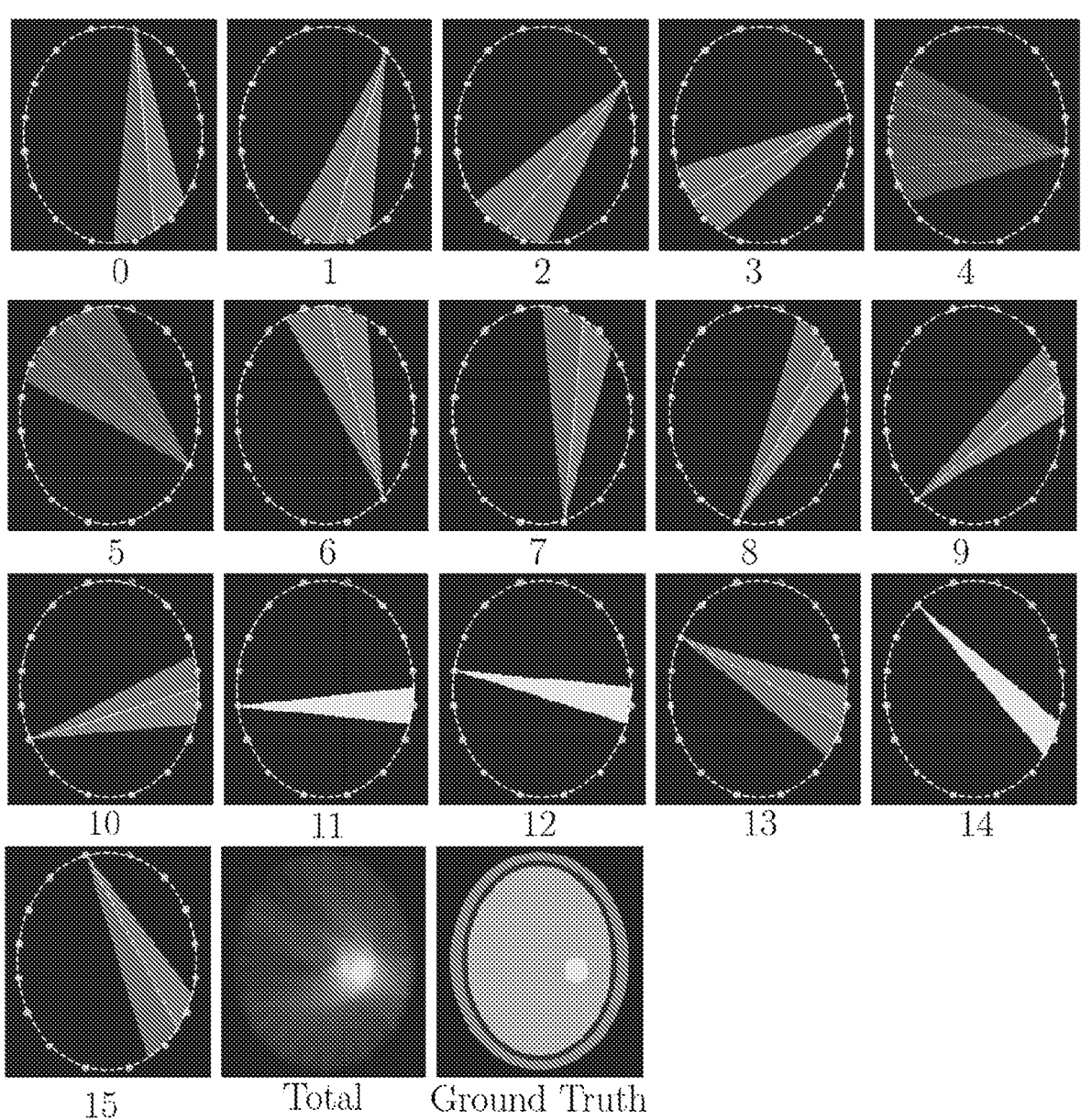
FIG. 6 includes schematic plan view images of the antenna array, illustrating processes for generating a composite or aggregate image ("Total") of the object by combining the 16 partial images ("0" to "15") for respective antennas, and a corresponding image showing the corresponding ground truth; comparison of the composite and ground truth images confirms that the microwave imaging apparatus and process can generate accurate images of internal features of objects.

After the partial-solution images from all nodes of the graph have been generated, they are then combined to generate a final predicted image of the target. Thus as illustrated in FIG. 6, the 16 partial images labelled "0" to "15" are combined to generate a composite image labelled "Total". In the described embodiments, the partial images are combined by simply summing individual 'pixel' intensities, although other methods may be used in other embodiments, including non-linear combinations based on prior knowledge, for example. Comparison with an image of the ground truth in FIG. 6 indicates that the composite image is an accurate representation of the ground truth, in terms of both size and location within the object.

Figure 7:
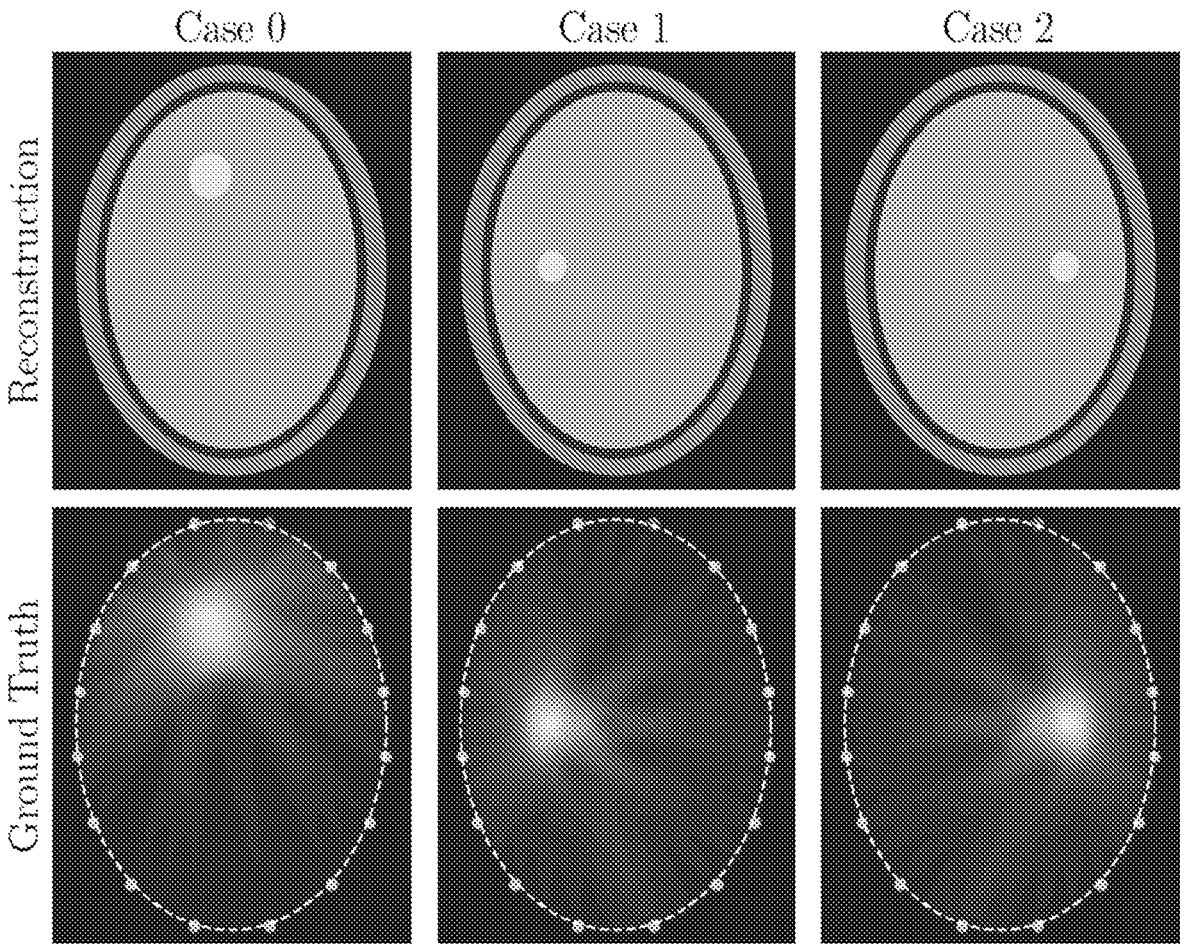
FIG. 7 includes three plan view images of respective different ground truths and respective composite images generated by the microwave imaging apparatus and process.

FIG. 7 illustrates the imaging performance of the imaging process for 3 different ground truths. In each case, the imaging process generates a composite image that accurately reflects the size and location of the anomaly.

It should be noted that although the particular methodology described above for encoding and decoding/generating images is convenient and performs very well, it will be apparent to those skilled in the art that alternative image encoding and decoding methodologies may be used in other embodiments without affecting the GNN model described below. Knowledge of the underlying physics is captured by the model itself, while the image encoding and decoding processes described above simply provide one way of expressing this knowledge, and do not affect how to capture that knowledge, which is greatly determined by the model architecture.

Graph Model

The inventors' motivation to use a GNN architecture for microwave imaging arose from the difficulty of encoding the antenna array in a neural net architecture. The lack of physical constraints necessitates larger data which is usually unavailable, which makes common models such as CNN, U-Net, MLP and RNN impractical. Furthermore, in an imaging setup with N sources placed uniformly around the imaging domain, the physical measurement learned for one source is largely applicable for the other sources, give or take a few differences. Accordingly, a geometric neural network is eminently qualified to capture the symmetries of the antenna array.

The general equation of message passing, which generalizes convolution to irregular domains, is as follows:

$$x_i^k = \gamma^k \left( x_i^{k-1}, S_{j \in N(i)} \left( \phi^k \left( x_i^{k-1}, x_j^{k-1}, e'_{ij} \right) \right) \right)$$

where $x_i^k$ are the features of node i in layer k, $\gamma$ is the update function that acts on the current node's features and summarized messages received from the neighbouring nodes (or "neighbourhood") $N$ (i), $S$ is a permutation invariant function, and $\phi$ is the message function that consumes: the features of the current node $x_i^{k-1}$, the features of adjacent node $x_j^{k-1}$, and the features of the corresponding connecting edge $e'_{ij}$. In the context of microwave imaging, a long time series is present at the edges (say $e_{ij}$). This is first pre-processed in the model with a Multi-Layer Perceptron ("MLP"), represented as "$\beta^1$", to generate a reasonably sized vector of features as expected in the message passing equation above. Notationally, $e'_{ij} = \beta^1 (e_{ij})$, and the $\beta^1$ function is shared across all edges of the graph to keep the model thin. The message function $\phi^k (x_i^{k-1}, x_j^{k-1}, e'_{ij})$ is also implemented as an MLP ("$\beta^2$") that processes the messages $M_{i,j}$, being the concatenation of the attributes of nodes i & j along with the corresponding edge attribute $e'_{ij}$. As described above, in the described embodiments the node attributes/features are the spatial locations of the antennas.

$$\phi^k = \beta^2 \left( \left[ x_i^{k-1} \middle| x_j^{k-1} \middle| e'_{ij} \right] \right)$$

$$M_{ij} = \left[ x_i^{k-1} \middle| x_j^{k-1} \middle| e'_{ij} \right]$$

Aggregation is used as the permutation invariant function $S$, however, an attention mechanism is applied to assign more weight to the more important messages prior to aggregation. In the described embodiment, this is done via yet another MLP, "$\beta^3$", with one node at its output to generate the weights $\alpha$. The expanded notation of this final layer is as follows:

$$\alpha_{i,j} = \frac{\exp LRelu (\theta M_{ij})}{\sum_{j \in N(i)} \exp LRelu (\theta M_{ij})}$$

where $\alpha_{i,j}$ is the resulting weight associated with each full message (i.e., the concatenation) $M_{i,j}$, $\theta$ represents the weight parameters of the $\beta^3$ MLP itself, which are again, shared across all nodes, and LRelu is the leaky variant of the Relu function.

These weights $\alpha_{i,j}$ are multiplied by the full messages $M_{i,j}$ before aggregation. Finally, the update function $\gamma$ (also referred to herein as the "localizer") is implemented as yet another MLP, "$\beta^4$", that generates the label codes. A flow-chart of the process ("the model process") implemented by the model is shown in FIG. 3, and the flow of data in this model, which amounts to a graph convolution, can be summarized as follows:

For each node i∈ $G$:
Summarize edge attributes for all $\{e_{ij}$ s. t. j∈ $N$ (i)$\}$
Construct full messages from the edge attribute and nodes attributes.
Perform message passing.
Compute attention factors from the full messages received on per-node basis.
Apply weights to the processed messages, using the attention factors.
Aggregate the weighted messages.
Pass the latter to the localizer layer to infer the label for the node i.

Note that it is sufficient to perform the above sequence of steps once because the graph is fully connected, and consequently a single pass is sufficient to the spread the information to all nodes from their neighbours.

EXAMPLE

Figure 8:
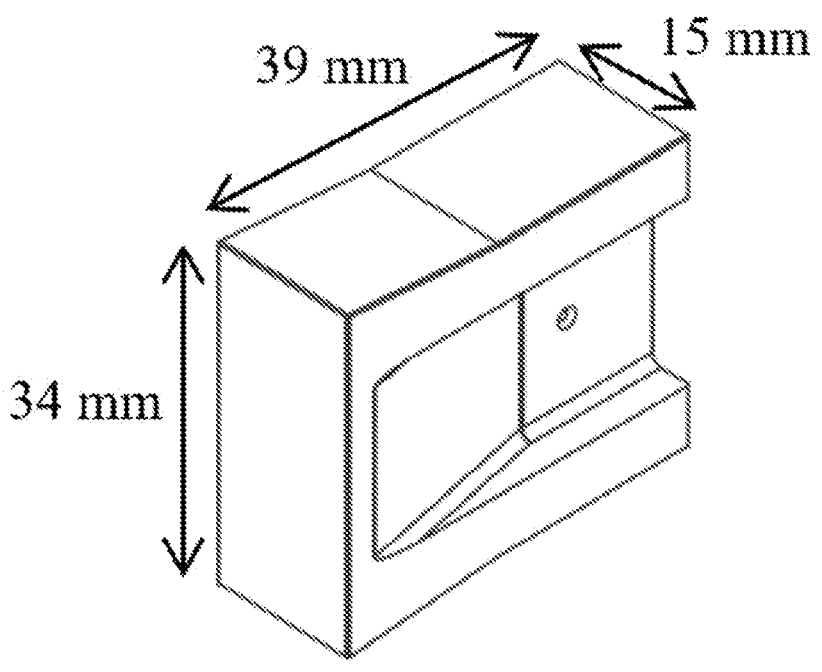
FIG. 8 is a perspective line drawing of a single microwave antenna of the apparatus, in accordance with an embodiment of the present invention.
Figure 9:
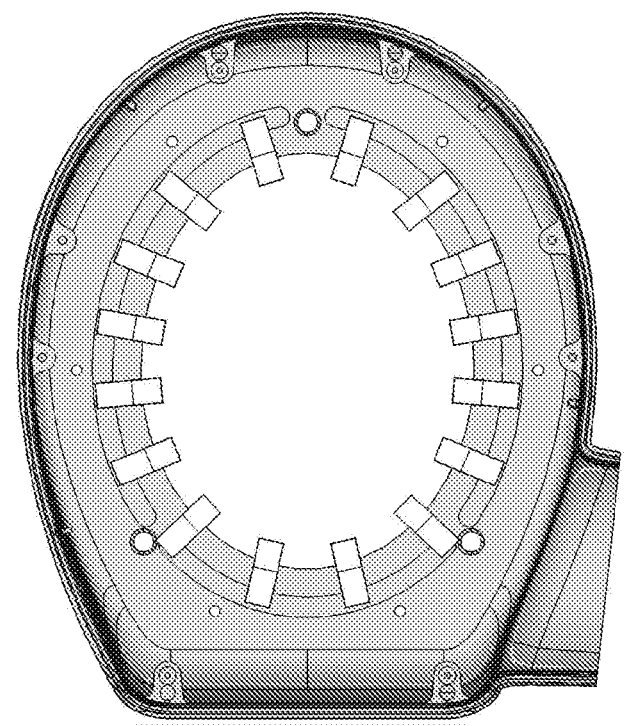
FIG. 9 is a plan view image of an elliptical array of 16 instances of the antenna of FIG. 8 attached to a rigid mounting structure configured to receive the head of a patient whose brain is to be imaged.

The model described above was implemented for a microwave brain scanning apparatus, as shown in FIG. 1, having an array of 16 waveguide antennas, as shown in FIG. 8, arranged in a symmetric manner around an ellipsoid rigid structure as shown in FIG. 9.

As shown in FIG. 1, the array of microwave antennas 105 is coupled to a data processing component 103 via a vector network analyzer (VNA) or transceiver 101.

The array of microwave antennas 105 is arranged to receive the head 104 of a patient whose brain is to be imaged, as shown, so that each antenna of the array can be selectively energised to radiate electromagnetic waves or signals of microwave frequency into and through the subject's head 104 to be scattered, and the corresponding scattered signals detected by all of the antennas 105 of the array, including the antenna that transmitted the corresponding signal.

As will be apparent to those skilled in the art, the vector network analyser (VNA) 101 energises the antennas as described above, and records the corresponding signals from the antennas as data (referred to herein as 'scattering' data) representing the amplitudes and phases of the scattered microwaves in a form that is known in the art as "scattering parameters" or "S-parameters". The VNA 101 sends this data to the data processing component which executes a microwave imaging process, as shown in FIG. 2, to generate information on internal features of the imaged object (e.g., brain clots, bleeding sites, and other features) that can (but need not) be used to generate images of those features. In the described embodiments, a VNA that has a large dynamic range of more than 100 dB and a noise floor below −100 dBm can be used to activate the antennas 105 to transmit electromagnetic signals across the frequency band of 0.5 to 4 GHz and receive the scattered signals from those antennas 105.

Although the data processing component of the described embodiment is in the form of a computer, this need not be the case in other embodiments. As shown in FIG. 1, the imaging apparatus of the described embodiments is a 64-bit Intel Architecture computer system, and the imaging processes executed by the electromagnetic imaging apparatus are implemented as programming instructions of one or more software modules 126 to 144 stored on non-volatile (e.g., hard disk or solid-state drive) storage 106 associated with the computer system. However, it will be apparent that at least parts of these processes could alternatively be implemented in one or more other forms, for example as configuration data of a field-programmable gate array (FPGA), or as one or more dedicated hardware components, such as application-specific integrated circuits (ASICs), or as any combination of such forms.

The apparatus includes random access memory (RAM) 106, at least one processor 108, and external interfaces 110, 111, 113, 114, all interconnected by a bus 116. The external interfaces include a network interface connector (NIC) 112 which connects the imaging apparatus to a communications network such as the Internet 120, and universal serial bus (USB) interfaces 110, 112, at least one of which 110 may be connected to a keyboard 118 and a pointing device such as a mouse 118, and a display adapter 114, which may be connected to a display device such as an LCD panel display 122. The imaging apparatus also includes an operating system 124 such as Linux or Microsoft Windows.

The imaging domain of the apparatus has major and minor axes of 344 mm & 300 mm respectively, and a height of 68 mm. The operating bandwidth of the antennas ranges from 0.5 GHz to 2.0 GHz. 751 frequencies with 2 MHz separation were captured via a 16-port vector network analyzer (VNA-M9800A) with a dynamic range of 110 dB. The power used was 10 dBm, which is well below the safety standard with regard to the specific absorption rate (SAR).

Figure 10:
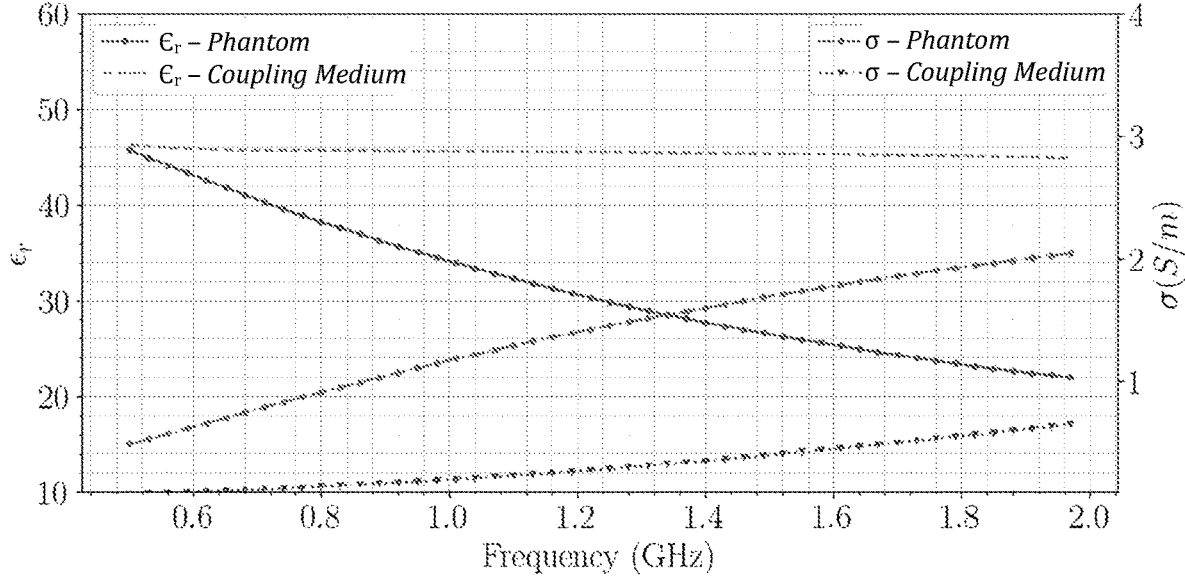
FIG. 10 is a graph of the dielectric properties (conductivity $\sigma$ and relative permittivity $\varepsilon_r$) of a head phantom, and a coupling medium applied between the phantom (or head) and the antenna array.

Lastly, a liquid coupling medium was used to match the background medium to the average electrical properties of the human brain. The dielectric properties of a phantom (representing the brain, as described below) and the coupling medium are shown in FIG. 10.

Figure 11:
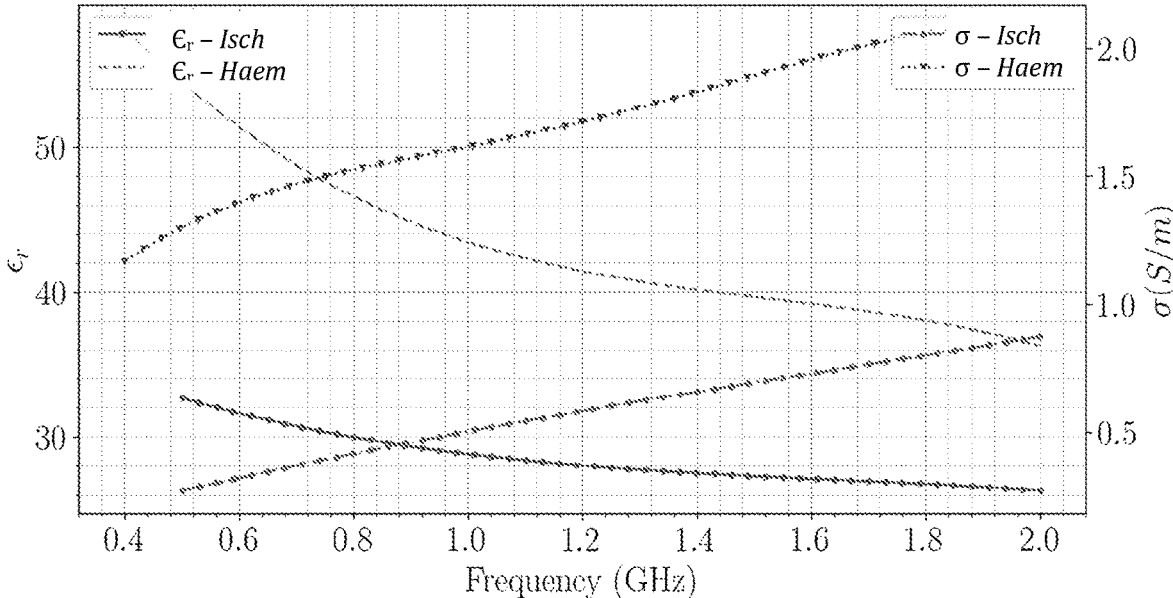
FIG. 11 is a graph of the dielectric properties (conductivity $\sigma$ and relative permittivity $\varepsilon_r$) of targets representing ischemic and haemorrhagic stroke regions in a human brain.
Figure 12:
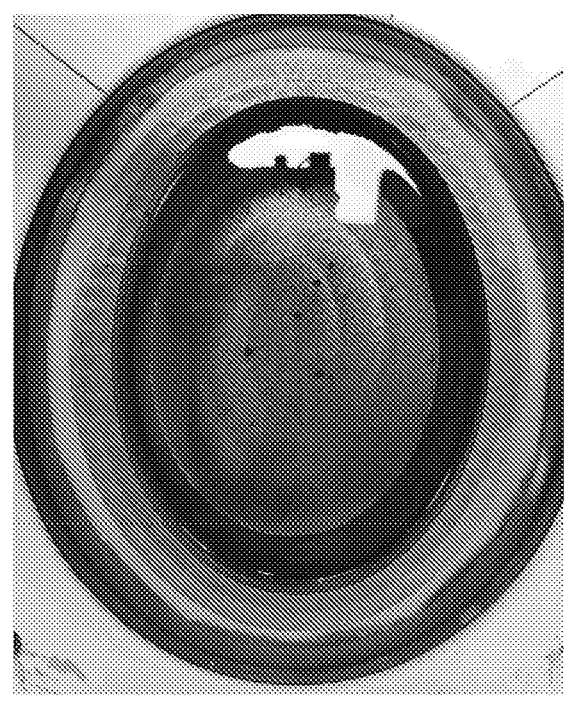
FIG. 12 is a plan view photographic image of the human head phantom.
Figure 13:
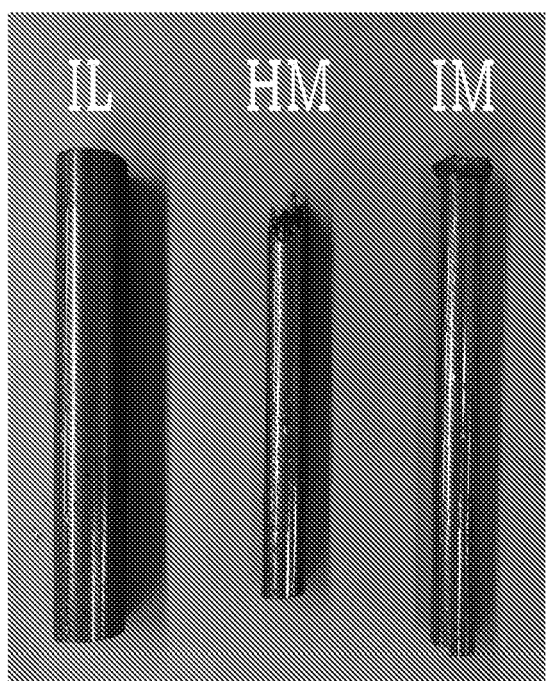
FIG. 13 is a photographic image of three targets representing (from left to right) a large ischaemic stroke region ("IL"), a medium haemorrhagic stroke region ("HM"), and a medium ischaemic stroke region ("IM")

The imaged object for this example was an ellipsoid phantom, as shown in FIG. 12, with two boundary layers to mimic the skin and skull dielectric properties, and homogeneous contents to replicate the average properties of the human brain. The targets of imaging interest are shown in FIG. 13, and were constructed to emulate two types of stroke, hemorrhagic and ischemic. The properties of a hemorrhagic stroke naturally follow those of blood, whereas an ischemic stroke causes a reduction in the permittivity of the affected tissues. FIGS. 9 is a graph showing the dielectric properties of those targets, and FIG. 11 is a graph showing the dielectric properties of the homogeneous phantom liquid and the coupling medium.

Figure 14:
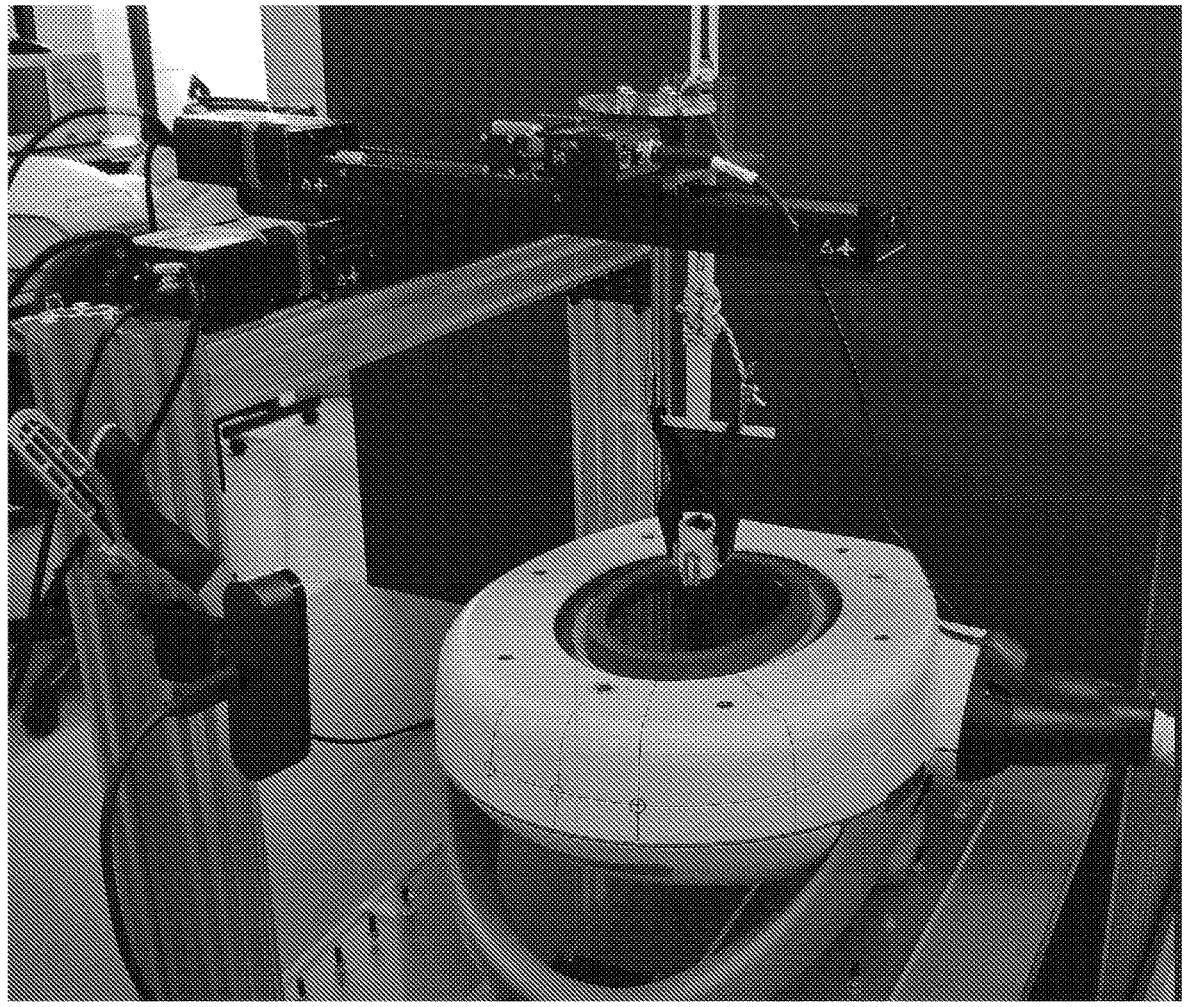
FIG. 14 is a photographic image showing one of the stroke targets of FIG. 13 disposed within the human head phantom of FIG. 12 and mounted to a CNC machine to allow random placement of the stroke target under computer control.

As shown in FIG. 13, the targets of interest were in the form of elongate cylinders having diameters of 20 mm or 30 mm in diameter. As shown in FIG. 14, a CNC machine was used to place the targets at random locations inside the phantom. The height of the target was also taken into account, and was made to change between −20 to +20 mm relative to the center of the antenna array. In total, 700 measurements were made with different combinations of the targets, target positions and target heights.

The experimental configuration described above resulted in a model with 2,432 parameters. Table 1 summarises the specifications of each component of the model.

TABLE 1

| Architectural details of model implementation | | | | |
|---|---|---|---|---|
| Module | Width | Activation | # Params. | O/P Shape |
| Edge Summarizer $\beta_1$ | 10 | Tanh | 2120 | (1, 10) |
| Attention Module $\beta_2$ | 14 | SoftMax | 15 | (1, 1) |
| Aggregator S | NA | NA | 0 | (1, 15) |
| Localizer $\beta_4$ | 11 | LeakyReLU | 297 | (1, 1) |
| Total | | | 2,432 | |

Evaluation

To evaluate the described model, the collected dataset was divided into two subsets according to a 80:20 split for training and testing purposes, respectively. The learning rate was set to 0.0005 with a batch-size of 5. In fact, the effective batch-size would be 5*16=80 because the graphical model is trained on a per node basis, and there are 16 nodes in each graph. A square error loss function was used with the Adam optimizer known to those skilled in the art. The training continued for 50 epochs before the loss plateaued. Table 2 below summarises the configurations of the 5 different test cases.

TABLE 2

| Test cases specifications (radius, height (Z) and position (XY) are in mm units) | | | | |
|---|---|---|---|---|
| Case | Type | Radius | Z | XY |
| 0 | Haem | 10 | −10 | (−36, −10) |
| 1 | Isch | 10 | −10 | (−12, 26) |
| 2 | Isch | 15 | −20 | (−24, −10) |
| 3 | Isch | 10 | 10 | (12, 50) |
| 4 | Haem | 10 | 0 | (12, −19) |

Figure 15:
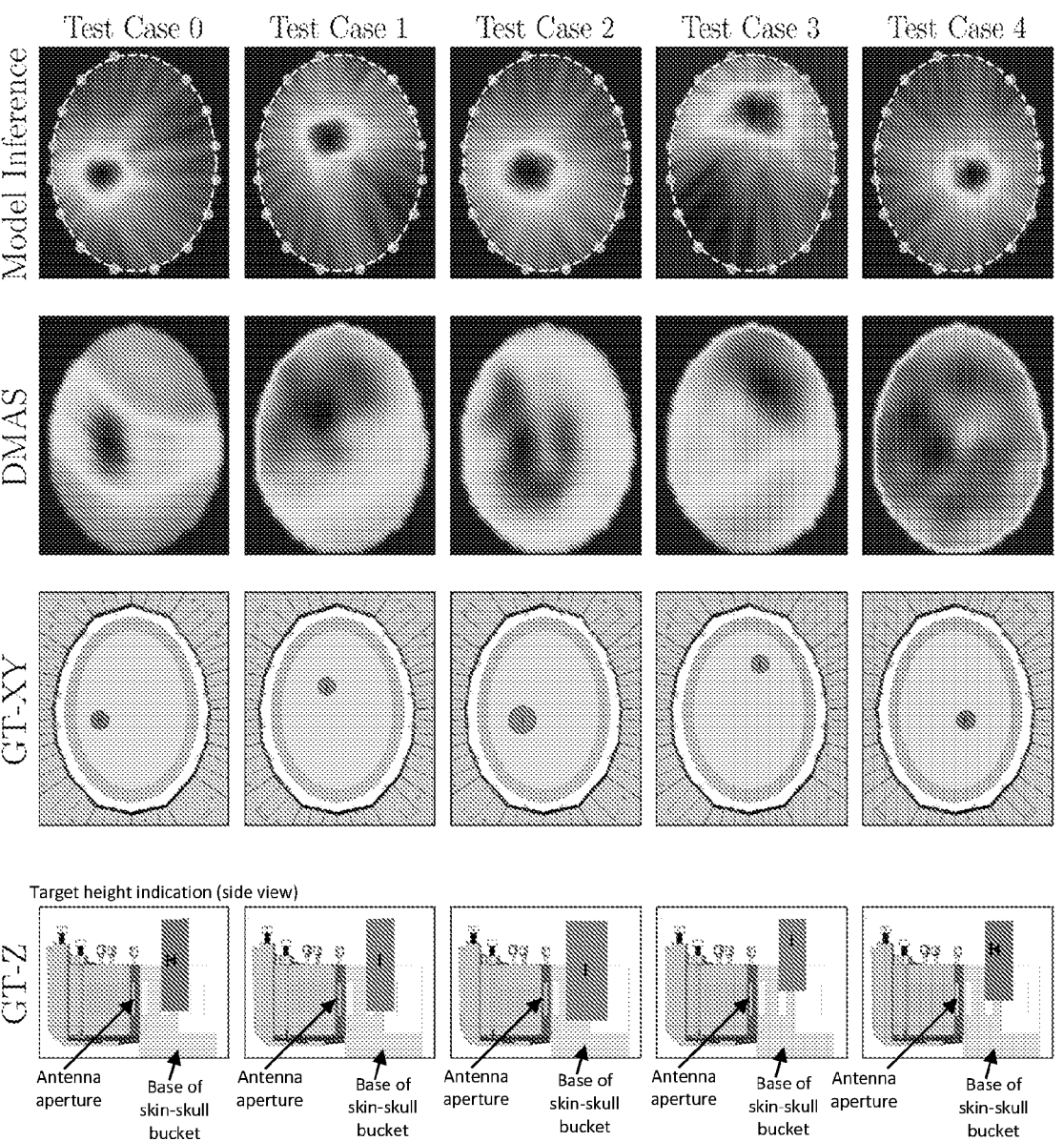
FIG. 15 demonstrates the performance of the microwave imaging apparatus and process as indicated by predictions on five test cases labelled "0" to "4" (top-row) and comparison with the corresponding ground truth cases (shown in plan view (showing target lateral position) in the third row, and side view (showing target height) in the bottom row), where blue and red colours indicate whether the target is ischemic or hemorrhagic respectively. The second row includes corresponding images generated by the standard prior art DMAS method, which clearly performs poorly relative to the apparatus of process described herein.

These configurations of the antenna array, phantom, and stroke targets are also illustrated schematically in the bottom row of FIG. 15, and in plan view in the second bottom row. The corresponding images generated by the apparatus using the trained model are shown in the top row of FIG. 15. Comparison of the ground truths of the third row with the images of the top row indicates that the model performance is reasonable in cases 0, 1 and 2 in terms of the location and size of the stroke target. In case 3 (rightmost column of Figure X), the target height is off the plane of the array (as seen in the bottom row 3‴), making it a challenging case. The impact of this relatively extreme spatial positioning on inference was to spread the target, resulting in an erroneously large size estimation. A similar impact on inference can be observed in case 4, where the target is deep within the phantom, i.e. close to the center of the array and far away from any antenna.

The results of the imaging process described herein can also be compared to corresponding results from the well-known DMAS algorithm, as shown in the 3rd row of Figure X. To ensure a fair comparison, an averaged signal from 200 measurements was used to remove clutter from the results of both processes. It can be seen from the results that although DMAS shows correct target positions in cases 0, 1, 2, and 3, there is substantially more clutter surrounding the target than in the images generated by the GNN-based process described herein. In particular, the conventional DMAS process provides an incorrect target position in case 4, in which the target is near the centre of the array, representing a deep target, where DMAS shows degraded performance owing to the increased path loss.

It will be apparent from the description above that the graph model based apparatus and process for microwave imaging described herein are able to efficiently generate accurate images of internal features of objects, in particular of anomalous features such as stroke regions in human brains. The geometric network of the model embodies the topology of the antenna array and remains light-weight while processing measured scattering parameters in an efficient manner. A relatively thin model with only 2,432 parameters proved sufficient to reconstruct accurate images of stroke regions.

The fact that partial solutions are generated at node level renders the model unaware of the total solution that follows aggregation. The obliviousness of the model to the overall solution provides at least the following benefits:

Because the aggregation of partial solutions can amount to an arbitrary total solution, this naturally endows the model with generalization capabilities.

for the same reason, this necessarily makes the model immune to overfitting.

The effective size of the dataset corresponds to the product of the number of measurements made by each node and the number of sensors making those measurements.

In the case of a mono-static antenna array, the underlying graph collapses into a set of disconnected graphs, each of which comprises a single node. Thus, the proposed model, while still applicable, will be reduced to a feed-forward model acting on individual signals at the node level. It is desirable but not necessary for the imaging array to be symmetrical. For example, the experimental imaging apparatus described above does not posses perfect circular symmetry by virtue of its ellipsoidal shape, and yet the model performs well.

Finally, it is also noted that the described model generalizes smoothly to three-dimensional arrays, unlike prior art models where fundamental changes are required.

Many modifications will be apparent to those skilled in the art without departing from the scope of the present invention.

The invention claimed is:

1. A computer-implemented process for electromagnetic imaging, the process including the steps of:

accessing scattering data representing measurements of electromagnetic wave scattering by internal features of an object, each of said measurements representing scattering of electromagnetic waves emitted by a corresponding antenna of an array of antennas disposed about an imaging domain containing at least a portion of the object, and as measured by a corresponding antenna of the array of antennas; and processing the scattering data to generate image data representing a spatial location and size of at least one internal feature of the object within the imaging domain;

wherein the processing includes applying a trained message-passing graph neural network (GNN) to a graph of nodes representing spatial locations of the antennas and edges representing the measurements.

2. The computer-implemented process of claim 1, wherein the step of applying the GNN includes summarizing the edges of the graph to reduce their number.

3. The computer-implemented process of claim 1, wherein the step of applying the GNN includes generating weights for messages of the graph by applying an attention mechanism to the messages, each message representing a corresponding pair of nodes of the graph and a corresponding edge for the pair of nodes.

4. The computer-implemented process of claim 1, wherein the step of applying the GNN includes applying an update function to weighted messages of the graph to generate inferred labels for nodes of the graph.

5. The computer-implemented process of claim 4, wherein the inferred label for each node represents quantitative measures of degrees of overlap between the internal feature of the object and respective lines joining the corresponding antenna to respective others of the antennas.

6. The computer-implemented process of claim 5, wherein the step of processing includes generating a plurality of partial images of the internal feature of the object for respective nodes of the graph, and combining the partial images to generate the image data.

7. The computer-implemented process of claim 6, wherein each of the partial images represents one or more inferred measures of electromagnetic wave scattering by the at least one internal feature of the object for a corresponding transmitting one of the antennas and one or more respective others of the antennas for which the respective degrees of overlap are inferred to be greater than zero.

8. The computer-implemented process of claim 7, wherein each of the partial images is generated by determining, for each pair of the corresponding transmitting antenna and a corresponding one of the one or more respective others of the antennas, a corresponding geometric sector within the imaging domain weighted by a corresponding degree of overlap, and generating the partial image by combining the one or more weighted geometric sectors for the transmitting antenna.

9. A non-transitory computer-readable storage medium having stored thereon executable instructions that, when executed by at least one processor, cause the at least one processor to execute the process of claim 1.

10. An electromagnetic imaging apparatus having components configured to execute the process of claim 1.

11. An electromagnetic imaging apparatus, including:

an array of antennas configured to define an imaging domain for receiving an object to be imaged; and at least one processor configured to:

access scattering data representing measurements of electromagnetic wave scattering by internal features of an object, each of said measurements representing scattering of electromagnetic waves emitted by a corresponding antenna of an array of antennas disposed about an imaging domain containing at least a portion of the object, and as measured by a corresponding antenna of the array of antennas; and process the scattering data to generate image data representing a spatial distribution of at least one internal feature of the object;

wherein the processing includes applying a trained message-passing graph neural network (GNN) to a graph of nodes representing spatial locations of the antennas and edges representing the measurements.

12. The electromagnetic imaging apparatus of claim 11, wherein the step of applying the GNN includes summarizing the edges of the graph to reduce their number.

13. The electromagnetic imaging apparatus of claim 11, wherein the step of applying the GNN includes generating weights for messages of the graph by applying an attention mechanism to the messages, each message representing a corresponding pair of nodes of the graph and a corresponding edge for the pair of nodes.

14. The electromagnetic imaging apparatus of claim 11, wherein the step of applying the GNN includes applying an update function to weighted messages of the graph to generate inferred labels for nodes of the graph, wherein the inferred label for each node represents quantitative measures of degrees of overlap between the internal feature of the object and respective lines joining the corresponding antenna to respective others of the antennas.

15. The electromagnetic imaging apparatus of claim 11, wherein the step of processing includes generating a plurality of partial images of the internal feature of the object for respective nodes of the graph, and combining the partial images to generate the image data.

* * * * *